United States Patent [19]

Booker

[11] Patent Number: 5,744,955

[45] Date of Patent: Apr. 28, 1998

[54] APPARATUS AND METHOD OF DETECTING LOSS OF CROSS-SECTIONAL AREA OF MAGNETIC METALLIC STRENGTH MEMBERS USED IN CONDUCTORS SUCH AS ALUMINUM CONDUCTOR STEEL REINFORCED (ACSR) CONDUCTORS

[76] Inventor: James R. Booker, 11718 Walnut Hill Dr., Baltimore, Ohio 43105

[21] Appl. No.: 544,598

[22] Filed: Oct. 18, 1995

Related U.S. Application Data

[63] Continuation-in-part of Ser. No. 510,198, Aug. 2, 1995.

[51] Int. Cl.$^6$ ............................ G01N 27/82; G01N 27/90
[52] U.S. Cl. ........................... 324/240; 324/228; 324/262
[58] Field of Search ................................ 324/220, 221, 324/226, 228, 229, 230, 239, 240, 241, 242, 243, 262

[56] References Cited

U.S. PATENT DOCUMENTS

| | | | |
|---|---|---|---|
| 2,057,835 | 10/1936 | Karajan et al. | 324/229 |
| 2,897,438 | 7/1959 | Fearon | 324/221 |
| 3,241,057 | 3/1966 | Rall | 324/243 X |
| 4,070,625 | 1/1978 | Harpster | 324/239 |
| 4,218,651 | 8/1980 | Ivy | 324/262 |
| 4,546,316 | 10/1985 | Lang | 324/262 |
| 4,827,215 | 5/1989 | van der Walt | 324/242 X |
| 5,321,356 | 6/1994 | Weischedel | 324/240 |
| 5,357,198 | 10/1994 | Ando et al. | 324/262 X |

FOREIGN PATENT DOCUMENTS

| | | | |
|---|---|---|---|
| 921556 | 2/1973 | Canada | 324/228 |

*Primary Examiner*—Gerard R. Strecker
*Attorney, Agent, or Firm*—Francis T. Kremblas, Jr.

[57] ABSTRACT

A method and apparatus for detecting a loss in cross-sectional area of metallic reinforcing members having magnetic properties of a conductor indicating corrosion effects on the conductor. The method and apparatus comprises a tug component to provide the motive force to move a data collection component and a detector component along a length of conductor. The tug component further includes a rechargeable battery, a motor energizable by the rechargeable battery, a guide wheel and tensioner assembly. Linked to the tug is a data collection component. In turn, a detector is linked to the data collection unit. The tug, data collection unit and detector all ride along the same conductor by a series of guide wheels and tensioners. The detector further includes a magnetic source spaced apart from an electronic coil winding. In use, a conductor is interpositioned between the magnetic source and electronic coil winding. The magnetic source is preferably energized to produce an alternating (e.g., oscillating or rotating) magnetic field which is directed at the conductor. The amount of magnetic field passing through the conductor corresponds to the cross-sectional area of the steel reinforcing strands of a conductor. The magnetic field recognized by the coil induces a varying voltage depending upon the cross-sectional area of the steel strands of the conductor through which the rotating magnetic field passes. The electronic coil may also be linked to a recording system such that the change in magnetic field induces a change in voltage in the coil which can be recorded on a strip chart, graph, CPU or other suitable data collection unit. The data collection component therefore may also include a relay system comprising a transmitter and receiver sufficient to send data streams and information to a ground surface when the unit is used above ground to analyze and test overhead conductors. An optional amplifier, band pass filter, and maximum and minimum type voltage meter may also be included.

14 Claims, 13 Drawing Sheets

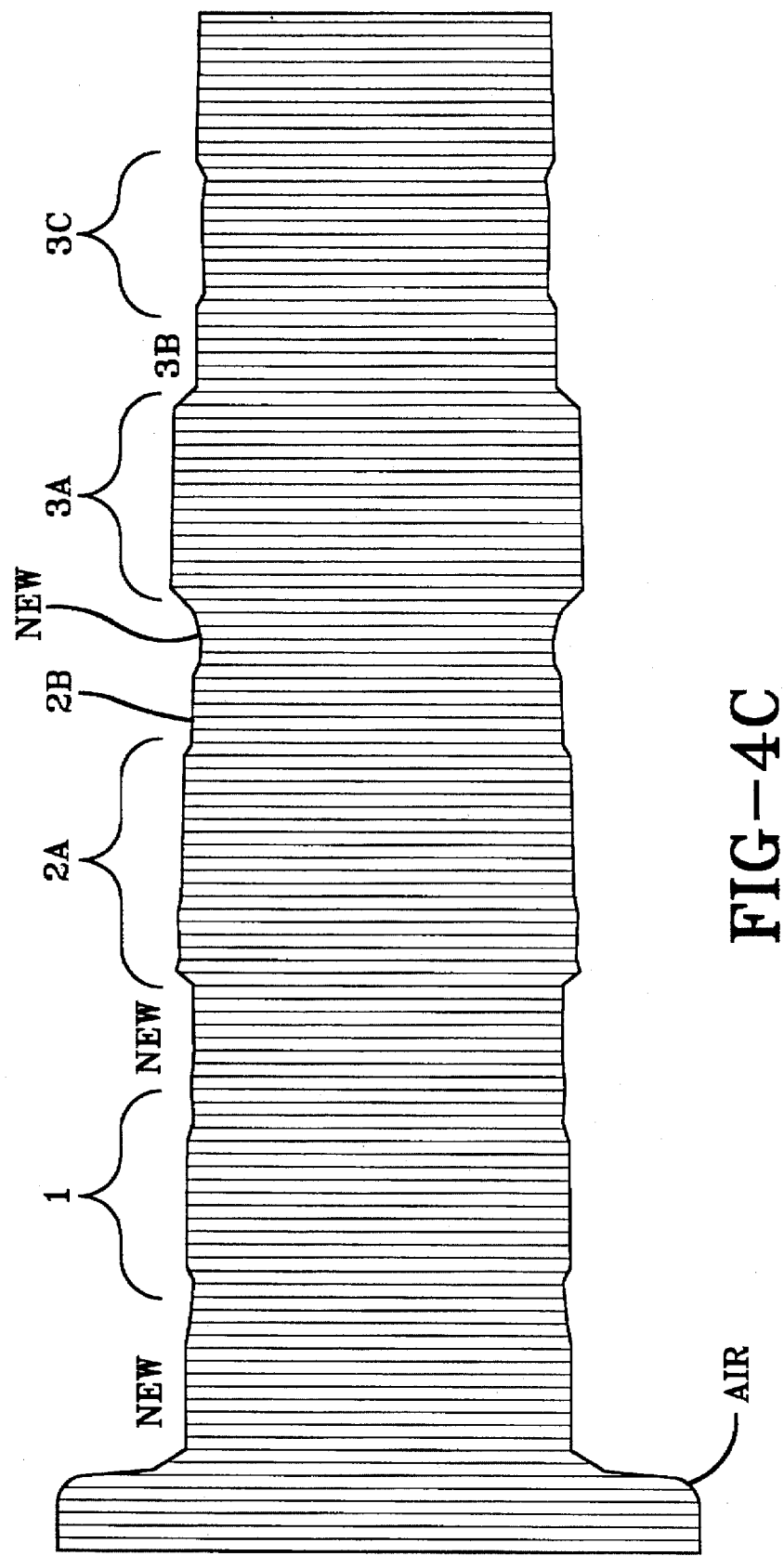

1

APPARATUS AND METHOD OF DETECTING LOSS OF CROSS-SECTIONAL AREA OF MAGNETIC METALLIC STRENGTH MEMBERS USED IN CONDUCTORS SUCH AS ALUMINUM CONDUCTOR STEEL REINFORCED (ACSR) CONDUCTORS

This is a continuation-in-part of copending application Ser. No. 08/510,198 filed on Aug. 2, 1995.

BACKGROUND OF THE INVENTION

1. Field of the Invention

The present invention relates generally to methods and apparatuses for detecting degradation of metallic conductors including, but not limited to, steel reinforced conductors, but more particularly to detecting a loss of cross-sectional area of the conductor or the steel reinforcing members of steel reinforced conductors due to the effects of corrosion, natural and industrial contamination and aging.

2. Description of the Related Art

Systems for the transformation of other types of energy (e.g., hydro, steam, etc.) into electrical energy, and the transmission of this electrical energy to the point of consumption may be referred to generally as electric power systems. Alternating current (AC) is generally used in modern power systems, because it may be easily converted to higher or lower voltages by means of transformers thereby enabling each stage of the electric power system to be operated at an appropriate voltage.

The frequency of electric power supply in the United States is 60 hertz (cycles per second). In other parts of the world, for example the United Kingdom, the power supply is 50 hertz. The frequency of a system is dependent entirely upon the speed at which the supply generator is rotated by its prime mover. Hence frequency control is basically a matter of speed control of the machines in the generating stations. Modern speed-control is very effective and hold frequency almost constant; deviations are seldom greater than 0.02 hertz.

In an AC system the voltage continually varies with time, at one instant being positive and a short time later being negative, going through 60 complete cycles of change in each second. Ideally a plot of the time change should be a sine wave. In a poorly designed generating equipment, or a poorly designed load such as a variable speed heat pump, harmonics may be present and the wave shape may resemble a sine wave but have erratic looking fluctuations in the wave print.

Practically all major power equipment is supplied by three-phase circuits. Three-phase circuits are essentially three single-phase circuits each of which has its own sine wave voltage. If phase balance is perfect, each of the three voltages is of the same magnitude but displaced in time from the others by one-third cycle. Modern three phase generators are designed to have almost perfect phase balance.

A typical electric power system consists of several principle elements including: the power station; a set of transformers to raise the generated power to the high voltages used on the transmission lines; the transmission lines; the substations at which the power is stepped down to the voltage on the sub-transmission lines; the sub-transmission lines; and the transformers that lower the sub-transmission voltage to the level used by the consumer's equipment.

In a typical system, the generators at the central power station typically deliver a voltage of from 1,000 to 26,000 volts (V). Higher voltages are usually undesirable because of difficulties of insulation and the danger of electrical breakdown and damage. This voltage is stepped up by means of transformers to values ranging from 138,000 V (138 Kilovolts or "KV") to 765,000 V (765 KV) for the primary transmission line (the greater the voltage on the line, the less the current and consequently the less the power loss, the loss being proportional to the square of the current).

At the substation, the voltage may be transformed down to levels of 69 KV to 138 KV for further transfer on the sub-transmission system to yet another set of transformers which steps the voltage down to a distribution level such as 2.4, 4.2, 15, 27 or 33 Kilovolts (KV). Finally, the voltage is transformed once again at the distribution transformer near the point of use to 240 V or 120 V (i.e., 110 volt household voltage). Thus, the central station of a power system consists of a prime mover, such as a water or steam terminal, which operates an electric generator.

A key component of the overall system, in order to transmit the power generated at the system to the end user or consumer, is the high voltage transmission line or sub-transmission line. The lines of high voltage transmission systems are usually composed of wires of copper, aluminum, copper clad or aluminum clad steel, and galvanized steel, which are suspended from a tall lattice work tower of steel by strings of porcelain insulators. By the use of clad steel wires and high towers, the distance between towers can be increased, and the cost of the transmission line thus reduced. In modem installations with essentially straight paths, high voltage lines may be built with, for example, as few as four towers to the mile (e.g., a 765 KV line). In some areas, high voltage lines are suspended from tall wooden poles spaced more closely together. For lower voltage sub-transmission and distribution lines, wooden poles are generally preferred rather than steel towers.

Long transmission lines have considerable inductance and capacitance as well as resistance. When a current flows through the lines, inductance and capacitance have the effect of carrying the voltage on the line as the current varies. Thus, the supply voltage varies with the load. Several kinds of devices are used to overcome this undesirable variation, in an operation called regulation of the voltage. The concept of electrical induction discovered by British Physicist Michael Faraday has been defined as the creation of an electric current in a conductor moving across a magnetic field. A similar, but inverse concept is the concept of reluctance.

Reluctance is the opposition offered in a magnetic circuit to a magnetic flux, but more specifically, is the ratio of the magnetic potential difference to the corresponding flux. Thus, a change in the conductor density, material, or other factors would affect the induction of electricity as well as present a reluctance change with respect to the aforementioned transmission and sub-transmission lines of a electrical power system.

The art to which the invention relates includes an apparatus and method of detecting galvanization loss on steel conductors or steel components of conductors. Such an overhead line galvanization detector has been referred to as a corrosion detector which is actually a misnomer because galvanization loss is believed to by some to merely mark the beginning of a corrosion cycle. In actuality, however, it has been shown that galvanization of steel members used in a water or other corrosive environments (e.g., considering the galvanic cell conditions created by water and metallic conductor components) has little if any effect as a corrosion retardant. One such device for detecting galvanization loss is a device called an "Overhead Line Corrosion Detector" marketed by Cormon LTD. of West Sussex in the United Kingdom.

The Cormon device and method of detecting galvanization loss includes an apparatus configured to rest on, engage, and travel along a transmission line or overhead conductor. The Cormon device incorporates a first drive component commonly referred to as a "tug" coupled to a data transmission unit. Both units are designed to be powered by rechargeable batteries. A detector head is coupled or linked to the data transmission unit and is pulled along with the assembly by the tug.

The tug component, therefore, serves merely as the motive force to pull the detection components along the length of the conductor (i.e., the data collection unit and the cylindrical collar-like detector head are moved along the conductor by the motorized tug). A transmitter is associated with the data collection unit and is believed to employ an RF data carrier signal to send the data collected by the detector head to a ground station or central processing unit (CPU).

The detector head or sensing head as it is referred to by Cormon is a hollow cylinder which clamps around the conductor. It contains a field winding and a pickup coil. When high frequency current is passed through the field winding, it generates a magnetic field surrounding the conductor. The magnetic field surrounding the conductor penetrates the conductor and induces eddy currents around the individual strands as the sensing head is pulled along the conductor.

The alternating flux induces a voltage in the pickup coil which is processed to give an in phase and quadrature output voltage, the magnitudes of which depend on the quality of the galvanized layer. Thus, the voltage differences realized by the pickup coil are attributable to the eddy currents induced within conductor as the sensing head is moved along the conductor. The detected voltage differences are correlated to the loss of galvanization through a series of algorithms, the manipulation of which is carried out by the CPU.

It is known that the Cormon device does not detect loss of cross-sectional area of steel reinforcing members of overhead conductors despite the name given the device by Cormon.

Considering the useful life of an overhead conductor is believed to be within the range of 10–80 years, and considering that many of the steel reinforced overhead conductors found in the United States, and many other countries of the world, were put in service in the 1930's and 1940's, it is particularly important to be able to determine the remaining useful life of such conductors. In addition, considering the extraordinary high cost of replacing such conductors and the attendant liability associated with energized conductor failure (i.e., conductors falling from their towers) it would be advantageous to invent a device capable of detecting the loss of cross-sectional area of steel reinforcing members of a conductor in a power transmission or sub-transmission line attributable to corrosion of the steel members. The reliability of the power system would be greatly enhanced if the near failures could be replaced before failure. Canadian Patent Number 921556, incorporated by reference as if fully set forth herein is directed to a method and associated apparatus for the electrical detection of flaws in materials. The Canadian device incorporates a plurality of current carrying coils which are placed beside the material to be tested. Some of the coils are then energized, and the resultant effect is detected by a pick up coil. The Canadian device differs significantly in structure and function from the apparatus and method of the present invention.

U.S. Pat. No. 4,218,651 granted to Ivy, incorporated by reference as if fully set forth herein, is directed to an apparatus for detecting longitudinal and transverse imperfections in elongated ferrous work pieces. The Ivy device differs significantly in structure and function from the apparatus and method of the present invention.

U.S. Pat. No. 2,897,438 granted to Fear on, incorporated by reference as if fully set forth herein, is directed to a casing joint detector. The Fearon invention is similar to the Ivy and Canadian devices, and it too differs significantly in structure and function from the apparatus and method of the present invention.

Accordingly, until now, there is no known method to measure the loss of cross-sectional area of steel reinforcing members of a conductor in a power transmission or sub-transmission line attributable to corrosion of the steel members.

SUMMARY OF THE INVENTION

The present invention is an apparatus and method for detecting a loss of cross-sectional area of steel strength members in aluminum conductor steel reinforced conductors commonly referred to as "ACSR" conductors. Of course, the present invention may also be utilized in conjunction with other types of conductors which incorporate steel members for added strength, wherein the steel members are subject to corrosion, natural and industrial contamination, aging, and thus associated strength losses.

The present invention is also useful for determining the loss of cross-sectional area of a shield or static line which are not energized. While structurally similar to lines associated with energized conductors, shield or static lines are essentially ground lines used in conjunction with overhead electrical distribution and transmission lines to effectively ground the electrical energy associated with lightening strikes and the like.

The apparatus of the present invention includes a motive component, a data collection component and a detecting component different in structure and function from the art to which the invention relates. The motive component which will also be referred to hereinafter as a tug component is comprised of a motor, a power source to energize the motor, and a series of guide wheels which maintain the tug component in proper motive alignment with the conductor. All of the tug components are attached to a common or interconnected housing.

The data collection component and detector components are pulled along the conductor by the tug. Thus, when the tug component is actuated, its drive system turns enabling the tug to drive the entire assembly (tug, data collection component and detector) along the conductor.

One of the key components of the invention is, therefore, the detector. The detector includes pulley-like wheel which maintains the proper alignment of the detector elements with the conductor. The detector also includes an electronic coil winding positioned adjacent to and in close approximation to the conductor when the detecting unit rests or is in operable engagement therewith. In this manner, the pulley wheels are preferably sized to correspond to a wide range of conductors yet allow the coil to maintain a predetermined optimal separation distance from the conductor to be analyzed. Opposite the coil and conductor to be analyzed is a source of an alternating (e.g., rotating) magnetic flux. In this manner, the conductor is interpositioned between the coil and the rotating magnetic flux.

The magnetic flux generating component of the preferred embodiment resembles a horseshoe or similar bi-polar magnet having oppositely designated poles for positive and negative charges. The magnetic source is rotated by an oscillating component which may be a simple motor sufficient to enable the horseshoe-like magnetic flux inducing magnet to rotate at an optimal predetermined rate of rotation. Alternatively, the magnetic source may comprise dual magnetic arrangement such that a pair of magnetic posts having opposite polarity are moved to and fro in an oscillating fashion to provide an oscillating magnetic flux.

The preferred geometry of the magnet partially comprising the alternating magnetic source is a cylindrical magnet with a bifurcated end having separate north and south poles. The preferred diameter of the magnet for the alternating magnet source is preferably commensurate with the width (i.e., diameter) of the steel strength member being analyzed.

In addition, it is preferred that the separation distance from the magnetic source to the conductor under test be minimized such that the magnetic flux emanating from the magnetic source is blocked to a greater degree of efficiency, and thus sensitivity of the inventive apparatus and system. When the magnetic source and conductor under test are in close proximity, the coil opposite the conductor is affected by the magnetic flux passing through the conductor and does not experience an induced voltage associated with the lines of magnetic force, which have a tendency to radiate outward along elliptical paths, passing around the conductor and not through it.

When energized, the motor spins the magnet about a central axis interpositioned between the poles. The spinning magnet induces a rotating, oscillating ("twisting") magnetic flux which impinges upon the conductor interpositioned between the magnetic flux generating device and the coil. Of course, the separation distance of the magnetic source and the conductor is preselected and may be adjusted according to the thickness of the conductor being analyzed. The coil, positioned on the opposite side of the conductor (recall the conductor is interpositioned between the twisting magnetic flux and the coil) detects the magnetic field passing through the conductor. The detected magnet field induces a voltage in the coil. The amount of voltage detected by the coil is recorded, and is known to be inversely related to the cross-sectional area of the steel reinforcing members within the conductor.

In the preferred embodiment the data collection component sends the data bit stream after being amplified on to a ground station or CPU. An RF carrier wave sending either AC or DC may be used as the medium to send the signal to the ground station or CPU where the incoming data stream may be recorded and illustrated by an oscilloscope type screen, strip chart, or stored magnetically in a computer for analysis.

The invention may also incorporate a voltage recording device to record the maximum and minimum voltages experienced (i.e., induced) by the coil winding. That is, a preferred recorder may also be a voltage meter capable of recording and storing maximum and minimum voltage information to enable the user to more efficiently extrapolate the useful life data of the conductor.

For example, the voltage induced into the coil for a "fresh" conductor (i.e., a conductor having a cross-sectional area equal to a new conductor as measured at the beginning of its useful life) could be a minimum baseline value. The voltage induced into the coil for a conductor of similar configuration with a known cross-section at the point of failure may be recorded as the maximum. Thus, if a conductor under test (an "aged" conductor, i.e., a conductor having a cross-sectional area measured at some time after the beginning of its useful life) were to induce voltage near the maximum value, the user may determine that a failure is imminent. Similarly, if the voltage associated with the test sample was below the maximum, and the time the conductor was in service was known, then the user may extrapolate to a point in time where imminent failure were to occur.

The invention may also include a data recording and acquisition component which includes a voltage recorder capable of detecting and storing a change in voltage induced into the coil by the alternating magnetic source can be recorded as a function of time, stored and downloaded into a CPU such as that associated with a PC. In addition, the preferred embodiment of the invention therefore also include support software to assist the operator in downloading the recorded data and manipulate it into a useful form.

Yet another component which may be used as part of the inventive system to partially comprise the data recording function and provide the associated structure of the invention is an oscillographic recorder having an oscilloscope and a strip chart function.

In use, when the apparatus is towed along a length of conductor by the tug component or by use of a rope from the ground, the detector may induce a voltage in the coil as described above. For example, if an air space (conductor absent) were interpositioned between the magnetic flux generating component and the coil, a base line voltage would be induced into the coil and recorded. If a conductor was interpositioned between the magnetic flux generating device and the coil, and this length of conductor is free of defects in the steel strands, the cross-sectional area of the steel strands would be 100% which would correspond to a second baseline voltage.

The disparity between the first and second baseline voltages creates the continual on which a loss of cross-sectional area of the steel reinforcing strands or the integrity thereof can be measured. For example, if a length of aged or partially degraded conductor were interpositioned between the magnetic flux generating device and the coil, a third baseline voltage would be recorded. This third baseline would fall somewhere between the first and second baseline values corresponding to 0% steel strands and 100% steel strands, respectively. Thus, the relative loss of cross-sectional area of the steel reinforcing strands would be detected and calculated.

If the inventive device was moved along a length of conductor, the varying voltages would yield critical information as to the existence, or lack thereof, of weak portions of the conductor due to a loss of the cross-sectional area of the steel reinforcing strands of the conductor. In this manner, it is conceivable that the user may accurately determine where an imminent failure of the conductor might occur. Furthermore, studies have shown that in a typical conductor having nineteen steel strands, if the cross-sectional area of the steel strands was to fall below the equivalent of seven (7) full "healthy" strands, a serious failure condition exists.

Thus, the method of the present invention is closely associated with the operation of the apparatus of the present invention in the manner in which the loss in cross-sectional area of the steel strength members of the conductor affect the conductor's efficiency as well as provide the user with a means to identify where and perhaps when a failure might occur in the conductor.

This method of detection, while closely associated with corrosion of the steel reinforcing strands may also be utilized to detect steel strands which are inferior in production and, therefore, create a weak link in the conductor and transmission line chain when initially installed or manufactured. This type of information may be particularly useful if one were to use the apparatus of the present invention and perform the method of the present invention to calculate and monitor useful life information of a variety of conductors from a point in time when they are first installed to a projected date of eventual failure.

This information may also be particularly useful to help the power industry budget for the great expense associated with replacing conductors and therefore possibly eliminate the unnecessary expense of prematurely replacing conductors which still possess a quantitatively significant useful life.

To that end, it is important to point out the distinction between the invention and the art to which the invention relates. For example, with respect to the Cormon device described above, a loss of galvanization provides no insight as to the loss of the integrity of the steel strength members, eventual failure, or any indication as to when a conductor must be repaired or replaced. Recall, loss of galvanization is believed to be the starting point at which corrosion might occur, but provides no information whatsoever as to the existing strength or lack thereof of the steel reinforcing members associated with the conductors.

An optional amplifier may be connected downstream from the coil so that the voltage reading picked up by the coil can be amplified to enlarge the peaks and valleys of the strip chart, or other data acquisition or collection component. An optional band pass filter may be provided to eliminate the vibrational harmonic readings associated with sixty (60) hertz (Hz) and the multiples of 60 Hz (e.g., 180 Hz., 300 Hz., etc.), or any other suitable system such as the harmonics of a 50 Hz. system of the United Kingdom. Similarly, an optional max/min meter may also be incorporated into the present invention.

The present invention may be summarized in a variety of ways, one of which is the following: a detector for detecting a loss of cross-sectional area in a conductor having at least one metallic reinforcing member, comprising: an attachment plate; a source of magnetic energy operatively mounted to the attachment plate and configured to emanate a magnetic flux; a coil winding operatively mounted to the attachment plate spaced apart from the rotatable magnetic source to define a receiving space therebetween, wherein the receiving space is configured to receive a conductor to enable the magnetic field to induce a measurable voltage within the coil winding even when the conductor is positioned in the receiving space and interpositioned between the source of magnetic energy and the coil winding.

The detector may further include a drive element to impart a rotational torque to the source of magnetic energy to cause the magnetic field to rotate; a recorder to record the voltage induced in the coil winding, an electrical connection means for electronically interconnecting the recorder to the coil winding, and a transmitter and a receiver to transmit information voltage information from the coil to the recorder by a radio frequency carrier signal and without the need for wiring to interconnect the recorder to the coil winding. The at least one metallic reinforcing member is at least partially comprised of a material selected from the group of materials consisting of steel, steel alloy and iron.

The detector may further include a housing to cover the coil winding and the source of magnetic energy, a power source for energizing the drive element, and wheel means for positioning the detector on a conductor. The source of magnetic energy may further comprise a magnet having a positive pole substantially parallel to a negative pole.

Due to the unique formation of the magnetic flux and the sensitivity at which the magnetic flux is blocked, the inventive system and device may be used to analyze line splices either in the field or the laboratory. When a splice of an ACSR conductor is made to join two ends of the conductors, a hydraulic press is usually used to press the splice over and into the conductor. In order for this splice to be made properly, the full hydraulic pressure specified must be used. If the full hydraulic pressure is not used, the resistance of this electrical connection increases and causes localized heating. The inventive technology detects this condition by sensing whether a loss of cross-sectional area has occurred or the conductor strands have separated into slightly birdcaged condition. The ability to detect such conditions enables the user to repress or remove the splice before its heating can cause a line failure.

The present invention may also be summarized as follows: a system for detecting a loss of cross-sectional area in a conductor having at least one metallic reinforcing member, comprising: a detector component; a data transmission component; a tug linked to the detector component and the data transmission component; drive means for supplying power to the tug, detector component and data transmission component, to enabling them to travel along a conductor; the detector further includes a source of magnetic energy configured to emanate a magnetic flux and direct the magnetic field toward at a coil winding spaced apart from the source of magnetic energy to define a receiving space therebetween, and enabling the coil winding to experience an induced voltage in response to the source of magnetic energy even when a conductor is positioned within the receiving space.

The electrical connection means of the system may further include a transmitter and a receiver to transmit information voltage information from the coil to the recorder by a radio frequency carrier signal and without the need for wiring to interconnect the recorder to the coil winding.

The present invention may also be summarized as follows: a method of detecting a loss of cross-sectional area of a conductor having a length and at least one metallic reinforcing member, the method comprising the steps of: providing a detector having a source of magnetic energy configured to emanate a magnetic flux, a coil winding spaced apart from the source of magnetic energy to provide a receiving space for a conductor to be interpositioned therebetween, and wherein the coil winding is configured to experience an induced voltage in response to the magnetic field; positioning a conductor in the receiving space interpositioned between the source of magnetic energy and the coil winding; energizing the detector; and recording the voltage induced in the coil winding.

The inventive method may also include providing a drive element to impart a rotation torque to the source of magnetic energy to cause the source of magnetic energy to rotate and emanate a rotating magnet field, providing a wheel means for positioning the detector on a conductor, moving the detector along the length of the conductor. The step of recording the voltage may further include the step of: transmitting the voltage information recorded by the recorder to a receiving station by a radio frequency carrier signal.

The present invention may also be summarized as follows: a method of forecasting the useful life of a conductor having at least one metallic reinforcing member based on a known minimum cross-sectional area, wherein the conductor has at least one metallic reinforcing member, comprising the steps of: providing a detector for measuring the cross-sectional area of the at least one metallic reinforcing member; measuring and recording the cross-sectional area of the at least one metallic reinforcing member at the beginning of the life of a conductor; measuring and recording the cross-sectional area of the at least one metallic reinforcing member at any time after the beginning of the life of a conductor; comparing the recorded cross-sectional area of the at least one metallic reinforcing member taken at the beginning of the life of a conductor to the cross-sectional area of the at least one metallic reinforcing member taken at any time after the beginning of the life of a conductor; determining the amount of loss in cross-sectional area of the at least one metallic reinforcing member and determining the amount of time that has passed between the measurement of the cross-sectional area of the conductor at the beginning of the useful life of the conductor and the measurement of the cross-sectional area of the conductor after the beginning of useful life of the conductor; and extrapolating from the combination of: (i) the amount of lost cross-sectional area of the conductor and the amount of time determined to have passed that is associated with the loss of cross-sectional area, and (ii) the known minimum cross-sectional area of the conductor, to determine the useful life of the conductor.

Therefore, numerous objects, features and advantages of the present invention exist, and only a sample of those objects, features and advantages are set forth herein.

It is an object of the present invention to provide an apparatus for detecting corrosion in a conductor.

It is an object of the present invention to provide an apparatus for detecting a loss in cross-sectional area of a conductor wherein such loss is associated with corrosion, natural and industrial contamination, and aging.

It is an object of the present invention to provide an apparatus for detecting strength loss due to corrosion or other degradation of a conductor.

It is an object of the present invention to provide apparatus for detecting a loss in strength of a conductor.

It is an object of the present invention to provide an apparatus to assist in the prediction of the useful life of a conductor.

It is an object of the present invention to provide an apparatus for assisting in the determination as to when a conductor should be replaced or repaired.

It is an object of the present invention to provide a system for recording the relative location of the loss of strength of steel reinforcing members of a conductor.

These and other objects, features and advantages shall become apparent after consideration of the scope of the specification and drawings set forth herein. All such objects, features and advantages are part of and contemplated as within the scope of the present invention even though not specifically set forth.

BRIEF DESCRIPTION OF THE DRAWINGS

FIGS. 4A, 4B and 4C are actual strip chart printouts illustrating the resultant data collected by an embodiment of the present invention after actual use;

DETAILED DESCRIPTION OF THE PREFERRED EMBODIMENT(S)

Figure 1:
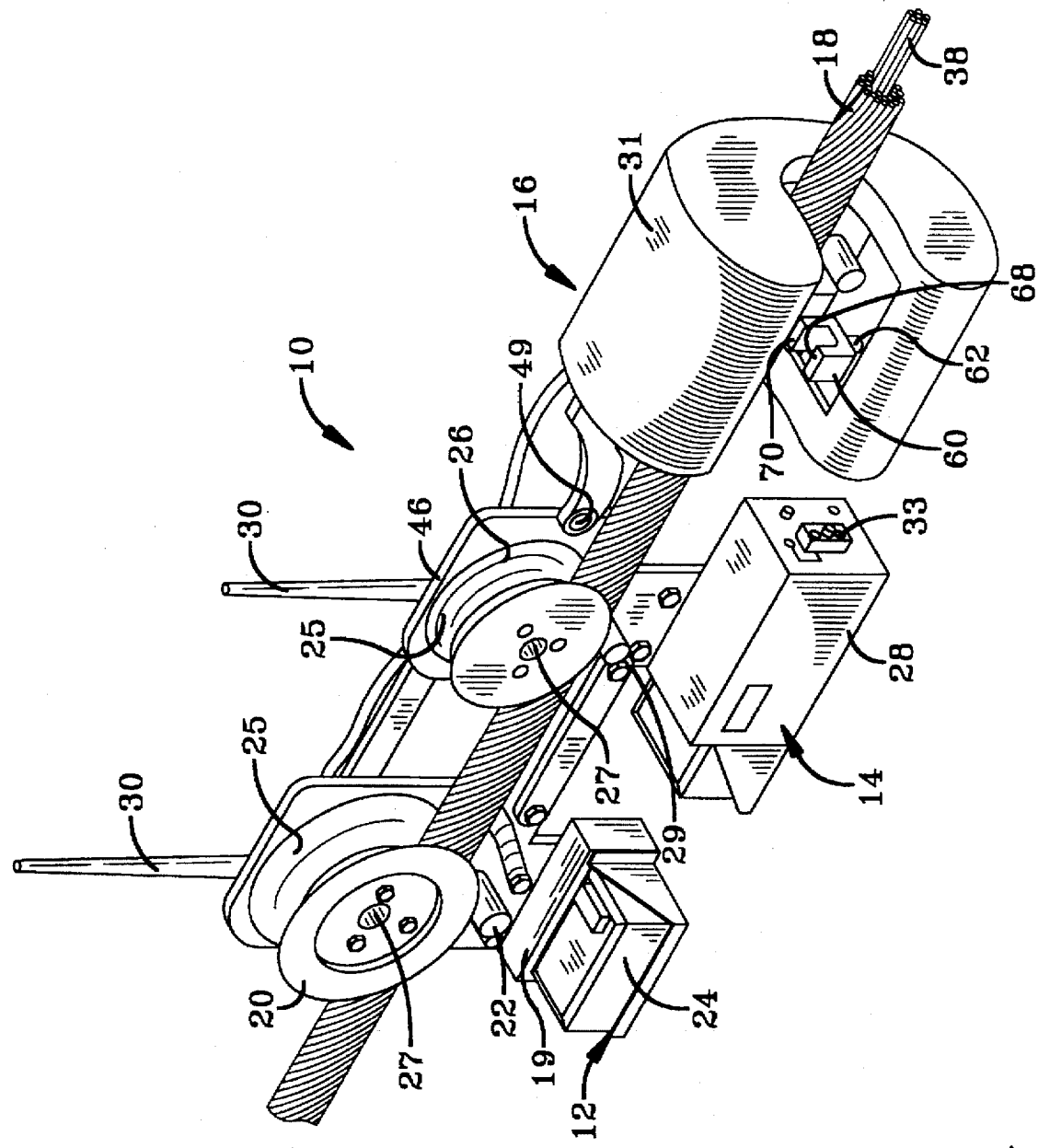
FIG. 1 is an elevated perspective view of an embodiment of the present inventive apparatus.

With reference to FIG. 1, an embodiment of the present invention is designated generally by the reference numeral 10. Embodiment 10 includes a tug component 12, a data collection and transmission component 14, and a detector designated generally by the reference numeral 16.

An embodiment of the tug component 12, data transmission component 14, and detector component 16 are operatively positioned on a conductor 18. Tug component 12 includes a housing 19, a guide wheel 20 and tensioner 22 to maintain the tug in communication with the conductor 18 during operation. A rechargeable battery 24 is provided to power the tug and provide the energy to power a drive motor (not shown) within the housing 19 sufficient to provide the electromotive force necessary to move the system along the conductor 18. The drive motor may be remotely controlled from the ground when the invention is used on an overhead conductor.

With respect to the collection and transmission component 14, a pulley wheel 26 and tensioner 29, similar to that provided with the tug component 12, is provided to maintain the detector in communication with the conductor 18. The guide wheel 20 and pulley wheel 26 have a trough 25 formed around their circumference like a conventional pulley wheel to enable the conductor 18 to rest therein and be interpositioned between the guide wheel 20 and tensioners 22 in the manner indicated in FIG. 1 in order to hold the conductor and tug in operative alignment therewith during use. The guide wheel 20 and pulley wheel 26 have a conventional axle 27 as shown in FIG. 1 enabling them to rotate around it. Similarly, with respect to FIG. 2, axle 27 enables the pulley wheel 50 to rotate it, and the hitch 44 to be attached thereto in the manner shown in the Figure. A transmitter (not shown) contained within the housing box 28 houses the internal components necessary to transmit data to a ground station or CPU (not shown). Antennas 30 provide the means through which signal transmission may be accurately achieved. An electrical connection 33 may also be provided to enable the exchange of electrical signals between components such as the relay of data from the detector 16 to the collection/transmission unit 14 or some other mechanism for recording data such as a CPU or strip chart recorder.

Tug 12 and data transmission component 14 may be of any suitable configuration but preferably is substantially similar or identical to the tug and data transmission component associated with the overhead line corrosion detector manufactured and sold by Cormon of West Sussex in the United Kingdom, and described above.

Figure 2A:
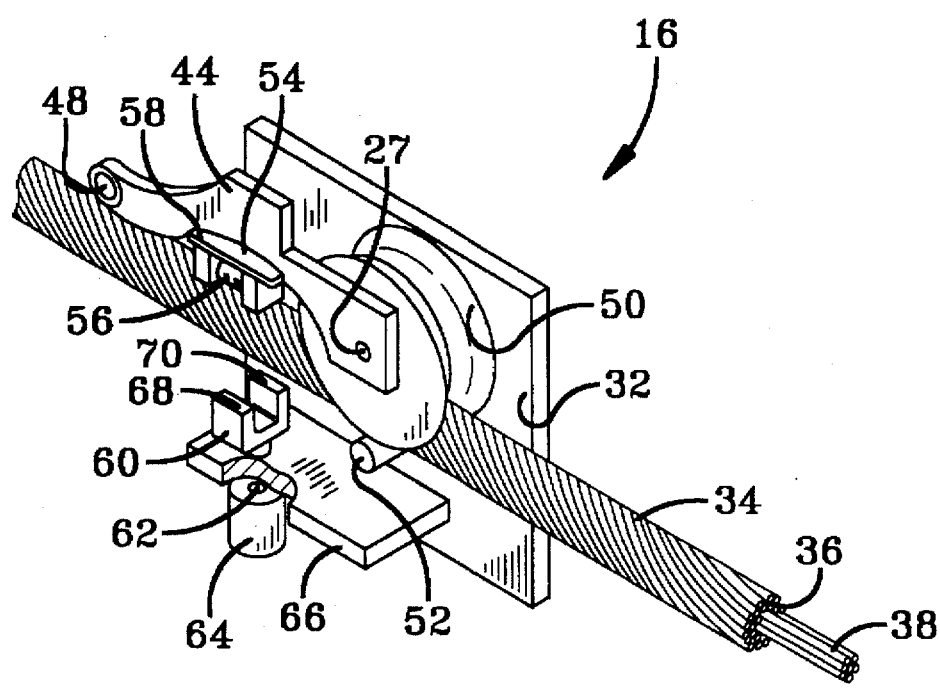
FIG. 2A and 2B is an elevated perspective view of embodiments of the detector component of the present invention shown in FIG. 1.
Figure 2B:
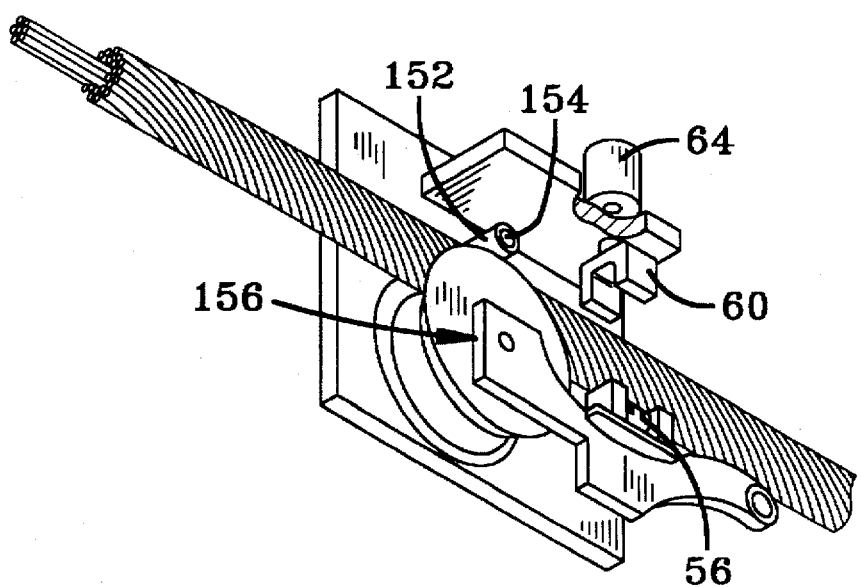

With reference to the detector 16, attention is now directed to FIGS. 1, 2A and 2B. Detector 16 includes a shielded housing 31 covering a baseplate 32 onto which several components may be mounted. A conductor 34 (18 in FIG. 1) is shown in relative operable alignment with the detector 16. The conductor 34 further includes a plurality of twisted strands 36 and 38 typically made from aluminum and steel, respectively.

Steel strands 38 provide the reinforcement necessary to the center of the conductor 34 to attain certain strength characteristics. That is, the steel strands 38 form the reinforcement of the core of the conductor 34 over which the aluminum strands 36 are wrapped.

Figure 3:
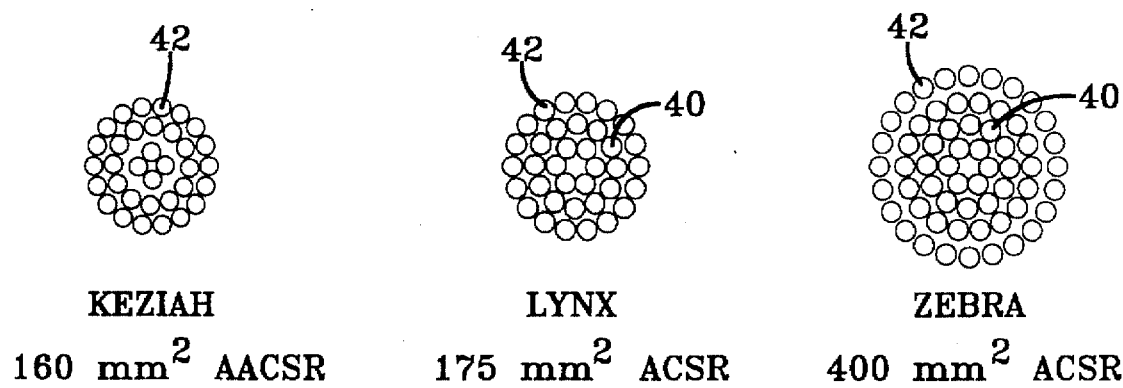
FIG. 3 is a representational cross-sectional view of several conventional ACSR conductors.

With brief reference to FIG. 3, several aluminum conductor steel reinforced (ACSR) conductors are illustrated in cross-section. The central starred configuration 40 is formed from the steel reinforcing strands 38 of FIGS. 2A and 2B. The outer circles indicate the cross-sectional area of the aluminum strands 42 corresponding to strands 36 of FIGS. 2A and 2B. Thus, it is common to provide a steel reinforced core consisting of seven tightly wound steel strands 40. The number of steel strands can be easily detected by counting the points from the star-like configuration of the core and considering a central strand is interpositioned between each of the points of the starred configuration.

Irrespective of the number of aluminum strands, and depending upon the size of the conductor used, it is common that ACSR conductors include one, seven, and nineteen strands surrounded by the aluminum strands to provide the added strength necessary for the conductor to maintain its integrity.

With reference to FIGS. 2A and 2B, a hitch 44 is provided as part of the detector 16. Hitch 44 attaches to rear plate or housing 46 of the detector 16 shown in FIG. 1. Thus, a preferred configuration of the hitch 44 includes a central aperture 48 through which a pivot pin 49 may be inserted to pivotally attach the hitch 44 to the data collection component 14 enabling it to be pulled along behind it by the tug 12 as it moves along the conductor 18 (or 34 in FIGS. 2A and 2B).

Attached to the hitch 44 is a pulley-like wheel 50 opposite a locking tensioner 52. The combination of the pulley 50 and locking tensioner 52 enables the conductor 34 to be operatively interpositioned therebetween and maintain an optimum contact enabling the detector to consistently and efficiently ride along conductor 34.

It is important to note that the detector 16 of FIGS. 1 and 2 is the same. The housing of FIG. 1 covers the detector in that figure. The hitch 44 emerges from the housing in the manner shown in FIG. 1 and is attached to the detector in the manner shown in FIG. 2. The hitch is shown bent in both FIGS. 1 and 2 in order to align it with the axis of the conductor, but other suitable configurations are allowable.

The detector rests on the conductor as shown in FIG. 2, and it is pulled by the tug of FIG. 1 by linking the detector to the tug by the connection of the hitch 44 to the rear plate 46 and the detector component. The housing is simply a shroud for the detector and is attached to the baseplate 32. The coil is operatively supported by this plate by virtue of the attachment to the hitch in the manner shown.

The detector 16 further includes a coil winding assembly 54. The coil winding assembly 54 includes a coil 56 and core 58. In addition, a magnetic source 60 is spaced apart and opposite from the coil 54 (and conductor 34). Magnetic source 60 includes a central axis which is parallel to a central shaft 62 which in turn is operably attached to a motor 64. Motor 64 provides a rotational torque to the shaft 62 enabling the magnetic source 60 to turn at an optimum rate of rotation.

A mounting plate 66 is provided to enable the magnetic source 60, shaft 62 and motor 64 to be operatively attached to the baseplate 32, and interposition of the conductor 34 between the coil 56 and magnetic source 60.

The embodiment shown in FIG. 2B is essentially the embodiment shown in FIG. 2A, but the orientation of the magnetic source and coil have been reversed such that the magnetic source is at the top or above the conductor and the coil is at the bottom or below the conductor. A roller 152 having a central axis 154 serves as stop for the conductor to ensure accurate and consistent separation of the conductor and the magnetic source. A tensioner pulley 156 therefore provides sufficient force against the conductor to clamp it within the gap between the roller 152 and pulley 156. Of course, the pulley 156 may be positioned above the roller 152 as shown in FIG. 2A and described above.

Furthermore, still other embodiments of the present invention are contemplated and are believed to be within the scope of the present invention. All such alternate embodiments, irrespective of the placement of the detector components and supporting structure with respect to the conductor, i.e., above or below the conductor, are believed to maintain the scope and spirit of the present invention without significant deviation from the function or utility of the invention.

With reference to FIGS. 2A, 2B and 4 for an exemplary description of the utility of the invention, a baseline reference of the recorded data printed out on a strip chart (FIG. 4) is formed by energizing the motor 64 enabling the magnetic source 60 to rotate. When this occurs, an alternating (rotating or oscillating) magnetic field or flux emanating from the opposing poles 68 and 70 of the magnetic source 60 induces a voltage in the coil 56. The induced voltage is recorded on a strip chart for graphical representation and visual identification.

Figure 4A:
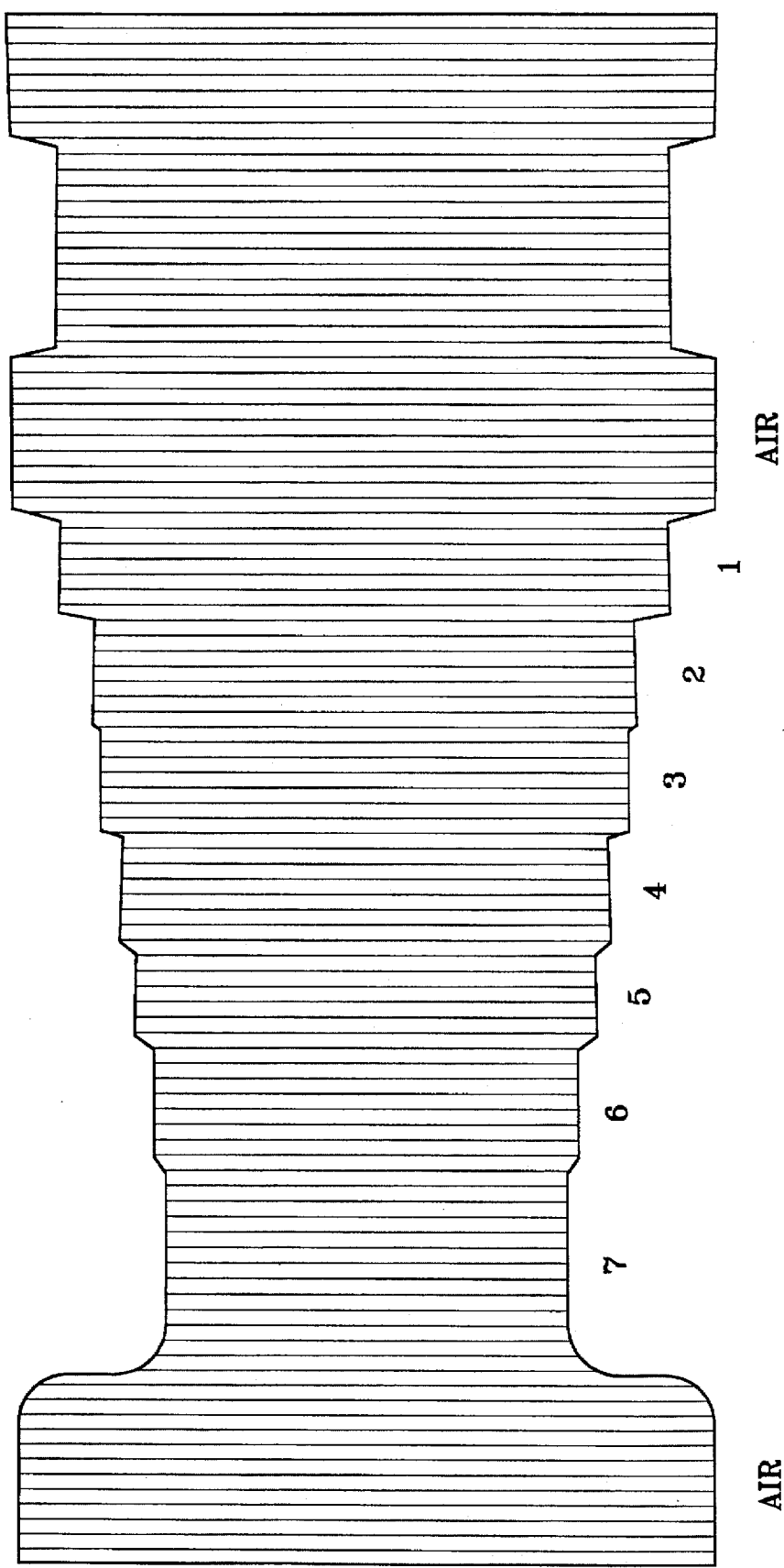

If the conductor 34 were absent from the space between the magnetic source 60 then coil 56, a strip chart printout of a certain width corresponding to the baseline of FIG. 4A would result. It is important to mention that FIGS. 4A and 4B is an actual strip chart of the operation of the device taken when an ACSR conductor having steel reinforcing strands is passed between the magnetic component 60 and coil 56 of the detector 16.

Referring to the width markings on the strip chart designated by the numeral "0" indicating that zero steel strands are present, the zero or baseline accurately corresponds to the baseline reading for air. As strands are added to the conductor the strip chart printout changes. For example, when one steel strand is added, denoted by the numeral "1", such that there are six strands missing, the strip chart nearly approximates the zero or baseline level for air, but is notably different. Similarly, the numerals "2" through "7" correspond to the number of steel strands present, with "7" denoting a complete conductor with seven steel reinforcing strands present. The strip chart printout for a seven steel strand conductor is the smallest corresponding to a notably lower voltage induced in the coil 54.

Figure 4B:
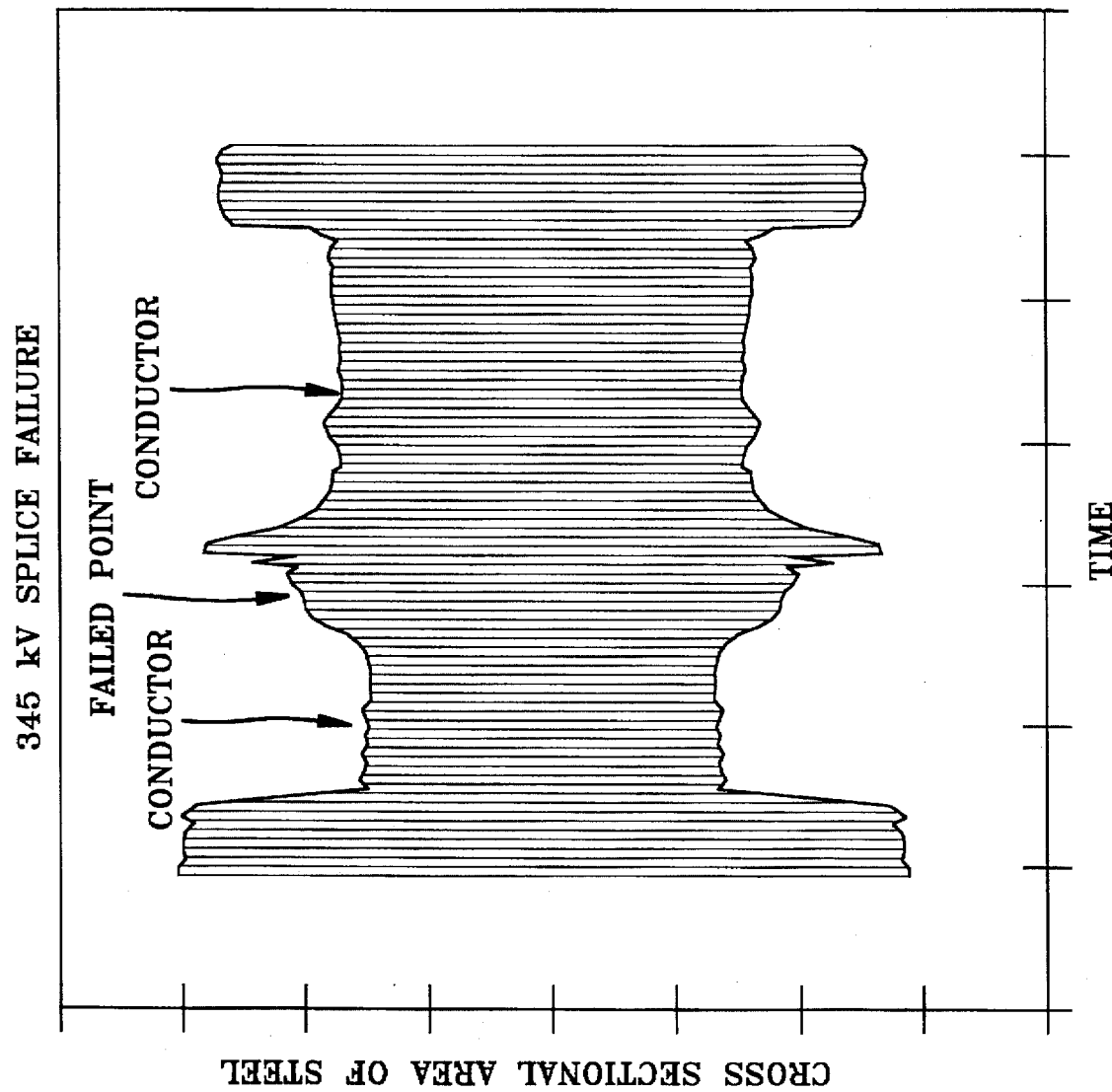

With reference to FIG. 4B, it is important to point out that the conductor being measured is a 345 KV line splice failure with 19 internal steel strands. It was determined through testing that of the nineteen (19) steel strands a cumulative strand cross-sectional area of seven strands led to a line failure. That is, while many of the original strands were present or simply broken at certain places, the cumulative cross-sectional area of all nineteen strands was less than seven "fresh" strands. As can be determined from the figure, the peaks of the strip chart correspond to the location on the conductor when the cross-sectional area was equal to seven strands. Similarly, where the valleys appear on the strip chart, they correspond to a substantially fresh segment of conductor having nineteen steel strands. However, as can be determined by the strip chart, even the nineteen strand portion of the old conductor does not dip to the level of the new conductor, thus it can be concluded that a minute loss in cross-sectional area had occurred.

Figure 5:
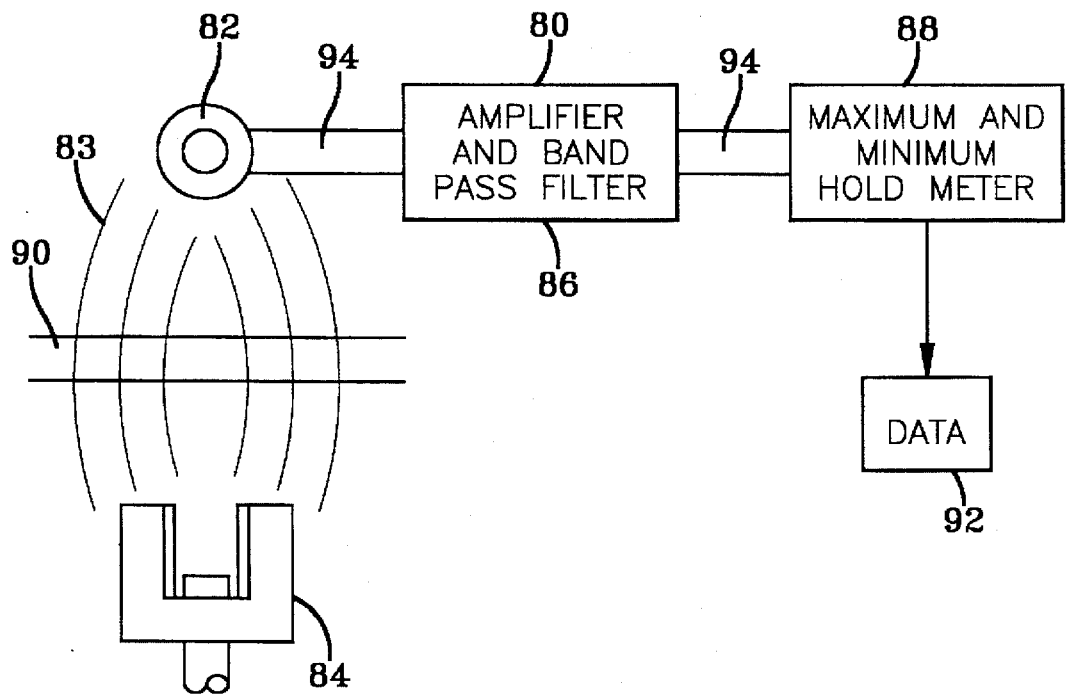
FIG. 5 is a schematic view of an embodiment of the present invention including electronic components for enhancing the resultant data generated or collected by the invention.

With reference to FIG. 5, optional electronic components may be added to the system in order to enhance the sensitivity and thus the accuracy of the inventive apparatus. An optional amplifier 80 is provided to enhance (amplify) the electronic signal induced into the coil 82 by the magnetic flux 83 generated by the magnetic source 84. In addition, incorporating a band pass filter 86 into the apparatus after the amplifier would tend to eliminate distortion from harmonic vibrations. Still further, an optional maximum and minimum type voltage meter 88 manufactured by companies such as John Fluke Mfg. Co., Inc. of Everett, Wash. model number 27, can be used to record the above-described base line readings or voltages.

By removing a single steel reinforcing strand from the conductor 90 and monitoring the readout on the max/min meter 88 of an embodiment of an amplified system, and continuing the strand removal progression until all of the available strands have been removed, the user may plot a substantially linear graph of the amount of voltage read in relation to the number of strands (or total cross-sectional area of all strands present) and attempt to predict the point in time when a failure is imminent or is likely to occur by using the data acquisition component 92. (See FIGS. 4A and 6).

If the voltage is known, as each strand is removed, the readings fall within the base lines determined by the max/min meter when a "fresh" conductor having full strength steel reinforcing members, and when the conductor contains no steel strands, the user may then use this information in a real time manner to determine the approximate location of weak segments of the conductor or those places where the minimal amount of steel reinforcing members exists.

The amplifier 80 is shown connected downstream from the coil 82 so that the voltage reading picked up by the coil 82 can be amplified to enlarge the peaks and valleys of the strip chart printout as shown in FIGS. 4A and 4B. The band pass filter 86 may be provided to eliminate the vibrational harmonic readings associated with sixty (60) hertz (Hz) and the multiples of 60 Hz (e.g., 180 Hz., 240 Hz.), (i.e., 50 Hz for the United Kingdom, and others for various other countries). Similarly, the max/min meter 88 is shown downstream from the amplifier 80 and band pass filter 86.

A shielded conductor 94 interpositioned between the coil 82 and amplifier 80, and the amplifier and max/min meter 88, is preferred in order to minimize distortion of the transmitted signals between the components. The max/min meter functions in the manner described above and will assist the user in practicing the method of the present invention. The data collection and analysis component 92 such as a CPU or, for example, a strip chart recorder is then linked to the max/min meter to provide an acquisition/recording and data manipulation function.

The invention may, therefore, also include a data recording and acquisition component which includes a voltage recorded such that the change in voltage induced into the coil by the alternating magnetic source can be recorded as a function of time, stored and downloaded into a CPU such as that associated with a PC.

A preferred embodiment of the voltage recorder is a "Data Recorder" manufactured by Telog Instruments, Inc. and is selected from the R-2100 series recorders. The voltage recorder (i.e., data recorder) is DC powered and may include its own DC battery or be connected to the DC power source used to energize the detector and/or the tug component of the invention.

In the preferred embodiment, the data recorder includes a wrap-around memory feature such that when the memory storage space of the recorder is full, the oldest data accumulated by the recorder is automatically overwritten. For example, if the recording time base of the data recorder were set at two hours to fill the memory storage capacity, the user of the invention may then download the stored data at any interval less than two hours. This feature may be particularly useful when the operator has several miles of strands of conductor to analyze and the conductors are elevated high tension electrical transmission lines.

Given that many high tension line towers incorporate several conductors spanning the distance between towers, the operators may analyze the entire set of conductor lines before climbing to ground level to download the data collected. Further, if the speed of the invention is known, and the span length of the conductors is known, the data recovered can be matched to the conductor analyzed so long as the order in which the conductors were analyzed is also known. Hence, the preferred data recorder also includes a programmable feature to allow the user to record data at a maximum, minimum, or average desired data recording interval.

In addition, the preferred embodiment of the invention therefore also includes support software to assist the operator in downloading the recorded data and manipulate it into a useful form. Like the data recorder, the preferred software is sold by Telog Instruments, Inc. under the model designation Telog S-21PC "Support Software".

A preferred motor used to rotate the alternating magnetic source is a 5200 rpm motor, sold by DC Gear, Inc. of New Hyde Park, N.Y., part number A3S35MCA3512. The 5200 rpm motor may also be geared down to throttle the rate of rotation to lower speeds such as 1000 rpm, 3200 rpm, or virtually any other desired rate of rotation depending upon the parameters of the system to be optimized. However, a rate of rotation of 5200 rpm, used in conjunction with a 300 turn thin coil formed from #29 copper wire has provided acceptable results.

The preferred geometry of the magnet partially comprising the alternating magnetic source is a cylindrical magnet with a bifurcated end having separate north and south poles. The preferred diameter of the magnet for the alternating magnet source is preferably commensurate with the width (i.e., diameter) of the steel conductor being analyzed. Therefore, it is believed that a larger or smaller magnet may be used and desirable when analyzing 1, 7, and 19 steel strand conductors. It is important to note, however, that virtually any diameter magnet and proper coil set will enable the system to function properly and provide useful results, and the motivation for selecting a magnet sized to correspond with the diameter of the coils is recommended for optimization purposes only and not by way of functional limitation.

Yet another component which may be used as part of the inventive system to partially comprise the data recording function and provide the associated structure of the invention is an oscillographic recorder having an oscilloscope and a strip chart function. One such device is sold by Yokogawa, model number ORM 1200.

The following examples are provided as information and are not intended, nor should they be construed, as limiting as to the scope of the present invention.

EXAMPLE 1: Conductor with Seven (7) "New" Steel Strands

Full or new steel strands extracted from a conductor were positioned between the working components of the detector and the voltages induced into the coil were measured as strands were removed.

| # of Strands | Voltage (mV) |
| --- | --- |
| 0 | 99.4 |
| 7 | 54.6 |
| 6 | 56.8 |
| 5 | 58.3 |
| 4 | 62.4 |
| 3 | 71.2 |
| 2 | 75.5 |
| 1 | 83.3 |
| 0 | 99.2 |

Thus, when seven partially corroded strands removed from an actual conductor are placed in the test apparatus, and the test voltage, for example, was 60 mV, one could conclude that the overall cross-sectional area of the steel strands is between the equivalent cross-sectional area associated with between four and five strands. As demonstrated by the example, a margin of error is + or −0.2 mV.

EXAMPLE 2: Conductor with Seven (7) Partially Corroded Steel Strands (FIG. 4A)

After first having removed the seven steel strands from an actual 345 KV conductor splice failure, the seven strands were analyzed with the following results.

| # of Strands | Voltage (mV) |
| --- | --- |
| 7 | 57.1 |
| 6 | 59.3 |
| 5 | 65.4 |
| 4 | 68.8 |
| 3 | 73.3 |
| 2 | 75.8 |
| 1 | 85.3 |
| 0 | 99.0 |
| 1 | 86.8 |
| 0 | 99.1 |
| 1 | 86.3 |
| 2 | 80.4 |
| 3 | 74.1 |
| 4 | 67.6 |
| 5 | 65.0 |
| 6 | 60.7 |
| 7 | 55.6 |

The discrepancy between the "first run" of the strands as compared to the "second run" as indicated by the separation point of "0" strands, is the measurement of the voltage was not recorded at precisely the same location of each strand along their individuals lengths. This phenomenon is best illustrated by examining the transitional section of the table where one strand was repeatedly removed prior to the second run. This data, therefore, supports the sensitivity of the apparatus as it is capable of detecting even minor variations in cross-sectional area of the strands being analyzed.

EXAMPLE 3: Length of Actual Conductor having Seven (7) Steel Strands (FIG. 4C)

The steel strands of the section of conductor were modified to present several distinct regions. The various regions are set forth in the table and are provided in this example to illustrate the sensitivity of the apparatus as it encounters a variety of decreases in cross-sectional area, single and multiple strand breaks. The inventive apparatus was mounted to and moved along the conductor by hand at a substantially constant velocity, and the output (i.e., induced) voltage in the coil was measured as a real time value.

Region 1: a three (3) inch length of conductor where a portion of the exterior surfaces of the steel strands were ground down to imitate corrosion of the outer surface of the steel strands.

Region 2: two steel strands are cut to form an opening or gap between the segments.
2A-two strands have a one half inch gap.
2B-one strand has a one and one half inch gap.

Region 3: three steel strands are cut to form an opening or gap between the segments.
3A-one strand cut for an opening of five inches;
3B-one strand cut for an opening of six inches; and
3C-one strand cut for an opening of seven inches.

| Region # | Voltage (mV) |
| --- | --- |
| 1 | 62.2 |
| new | 60.3 |
| 2A | 64.4 |
| 2B | 61.7 |
| new | 60.3 |
| 3A | 69.5 |
| 3B | 62.3 |
| 3C | 60.1 |
| new | 61.0 |

(The disparity of the induced voltages associated with the "new" conductors is believed to be attributable to the condition of the steel strands of the actual conductor, or other things such as the wheels used as part of the inventive system not exhibiting perfect roundness since most are made for conventional ropes and not steel conductors.)

Incorporating a pass filter when analyzing an energized conductor may be useful when the user desires to filter out the sixty (60) hertz (i.e., cycles per second) "noise" associated with the line current effect of the most common 60 hertz U.S. domestic power systems. Thus, different filters may be required or desired where the line current effect is not attributable to a 60 cycles per second system, but some other system such as the 50 Hz European system which includes the United Kingdom.

With reference to FIGS. 6–9, an embodiment of the present invention incorporating a 5200 rpm motor and 300 turn thin coil was used to repeat the analysis described in Example 1 set forth above. The inventive system was also amplified to operate at a much higher voltage (i.e., 0.8 to 1.6 volts) as opposed to the mV analysis of Example 1.

Figure 6:
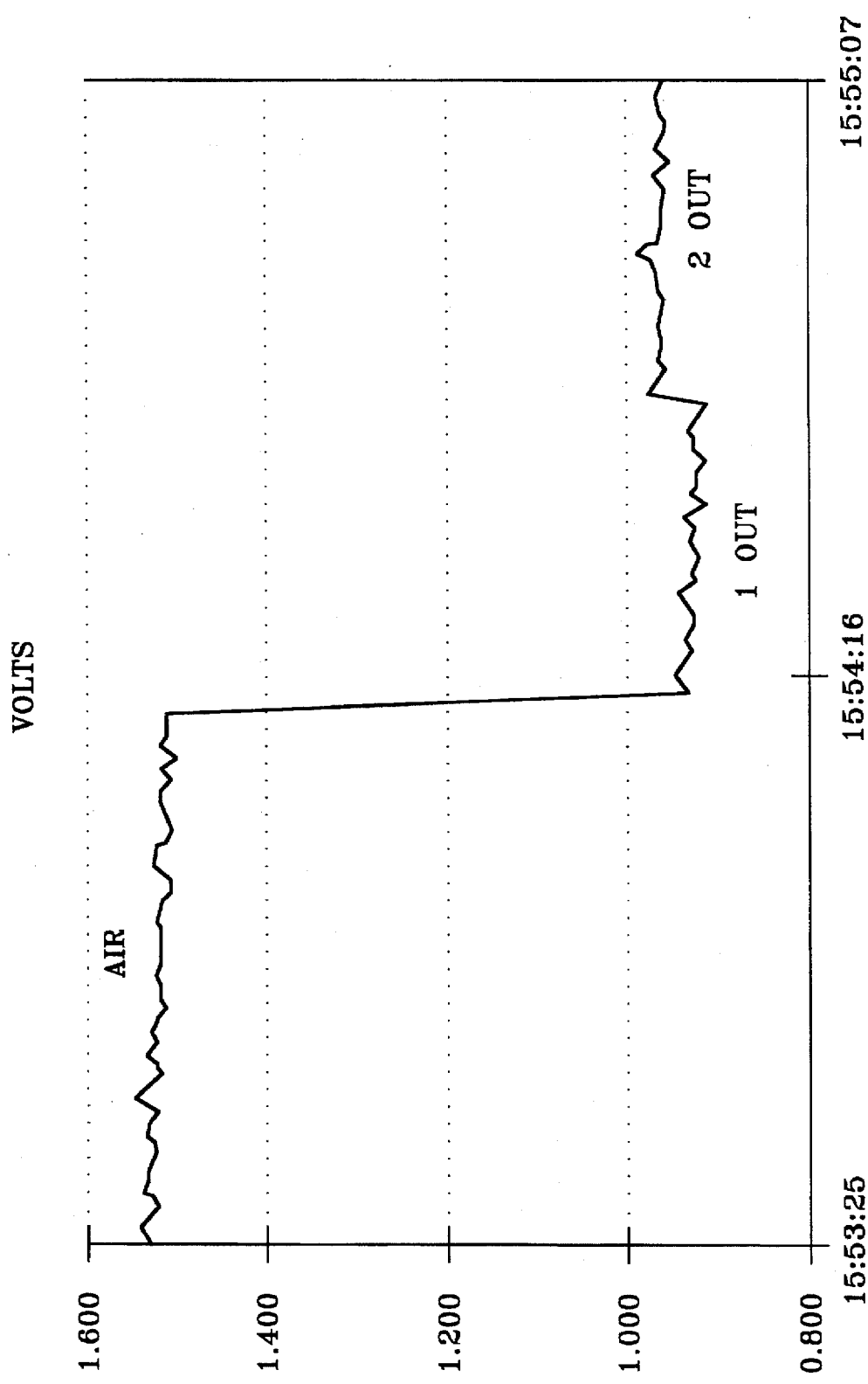
FIG. 6 is a printout of data recorded and printed by the data collection component of the invention and further illustrates the effect of voltage amplification on the inventive device when compared to FIG. 4C.

Referring to FIG. 6, when six of the seven strands were present (i.e., one strand removed as indicated by "1 out" shown on the Figure), the voltage induced into the coil was on the order of approximately 0.93 volts to 0.95 volts. When five of the seven strands were present (i.e., two strands removed as indicated by "2 out" shown on the Figure), the voltage induced into the coil by the rotating magnetic flux was approximately 0.96 volts to 0.98 volts. The waviness of the graph can be attributable to several factors such as the instability of the strands or a slight change in the separation distance between the strands and the detector components, when the strands were removed.

Figure 7:
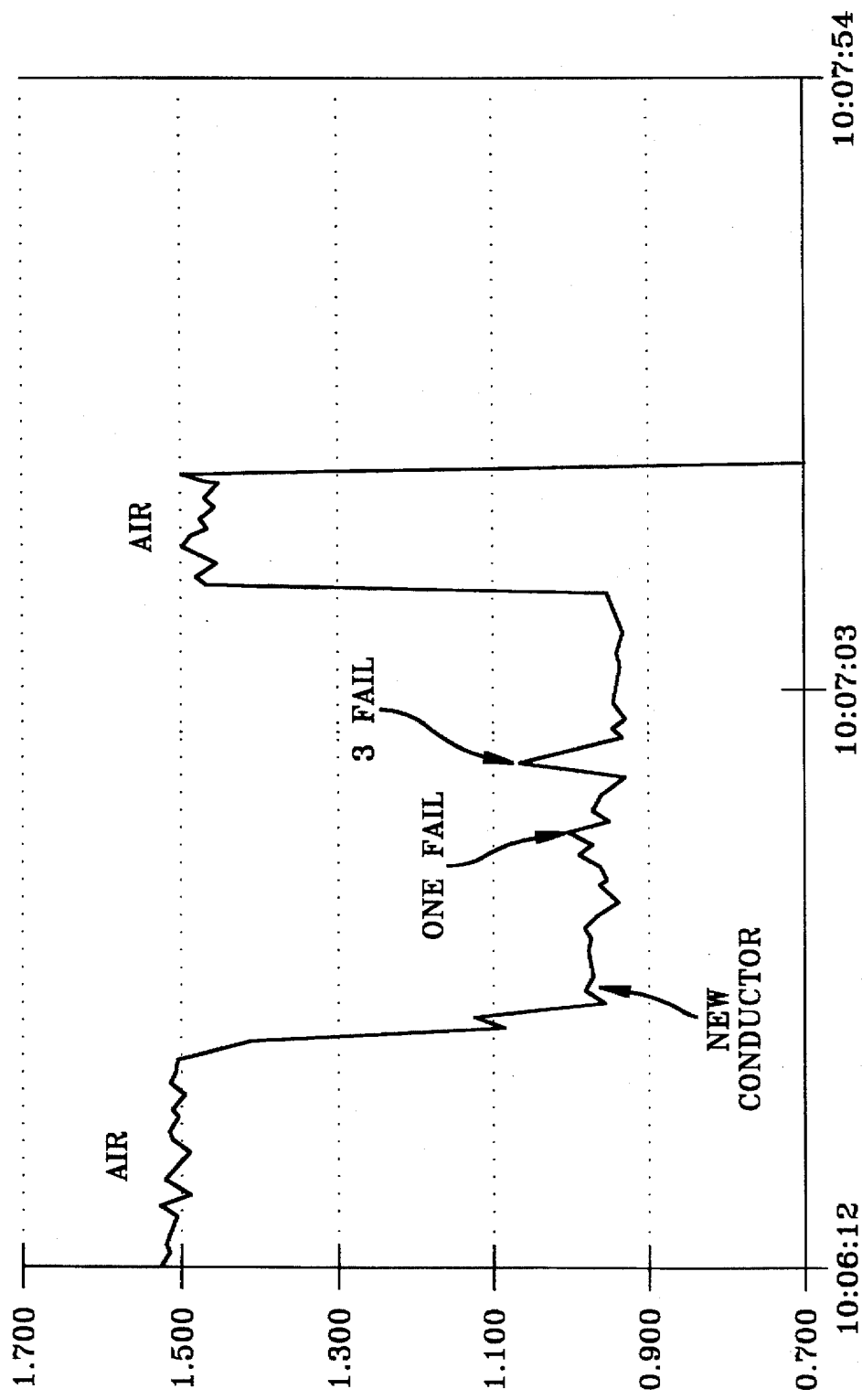
FIG. 7 is a printout of data recorded and printed by the data collection component of the invention and further illustrates the effect of amplification on the inventive device when compared to FIG. 4C.

Referring to FIG. 7, the actual segment of conductor used in conjunction with Example 3 set forth above was analyzed on the modified and amplified embodiment of the invention. As indicated on the Figure, sharp rises or "spikes" in the induced voltage are clearly detectable and are associated with a single steel strand break (i.e., "failure") and a three strand break or failure.

Figure 8:
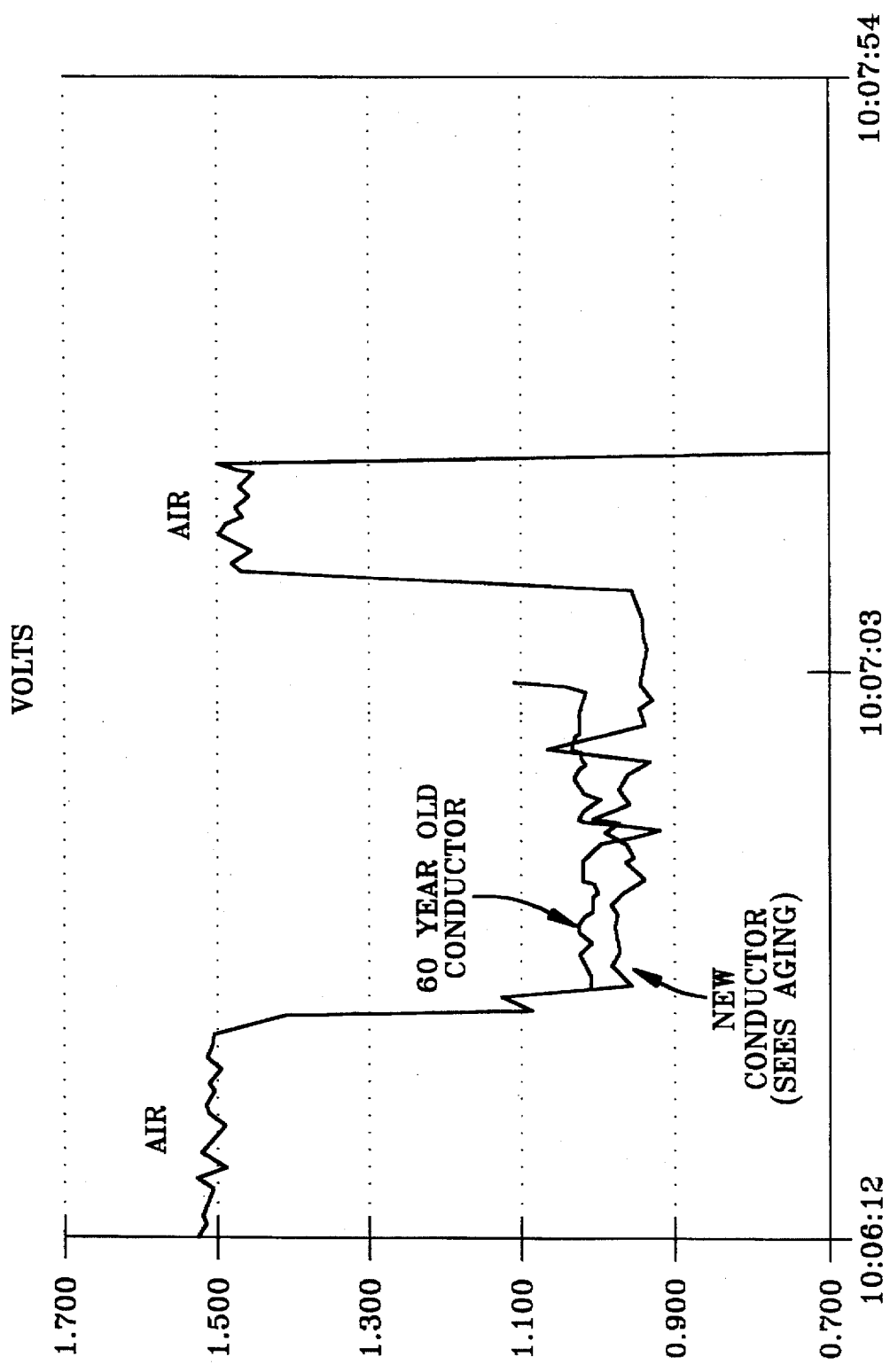
FIG. 8 is a printout of data recorded and printed by the data collection component of the invention and further illustrates the effect of amplification on the inventive device when compared to FIG. 4C.

Referring to FIG. 8, the conductor used in conjunction with Examples 2 and 3 were analyzed and the resultant data was collected, recorded and printed on the same graph. That is, the resultant data associated with a new conductor and a 60 year old conductor were analyzed and compared. As indicated by the gap of FIG. 8, there exists a clearly discernable gap between the data points associated with each sample. The gap is attributable to the effects of corrosion detected in the 60 year old conductor, and hence is further attributable to a loss of cross-sectional area and strength of the 60 year old conductor.

Figure 9:
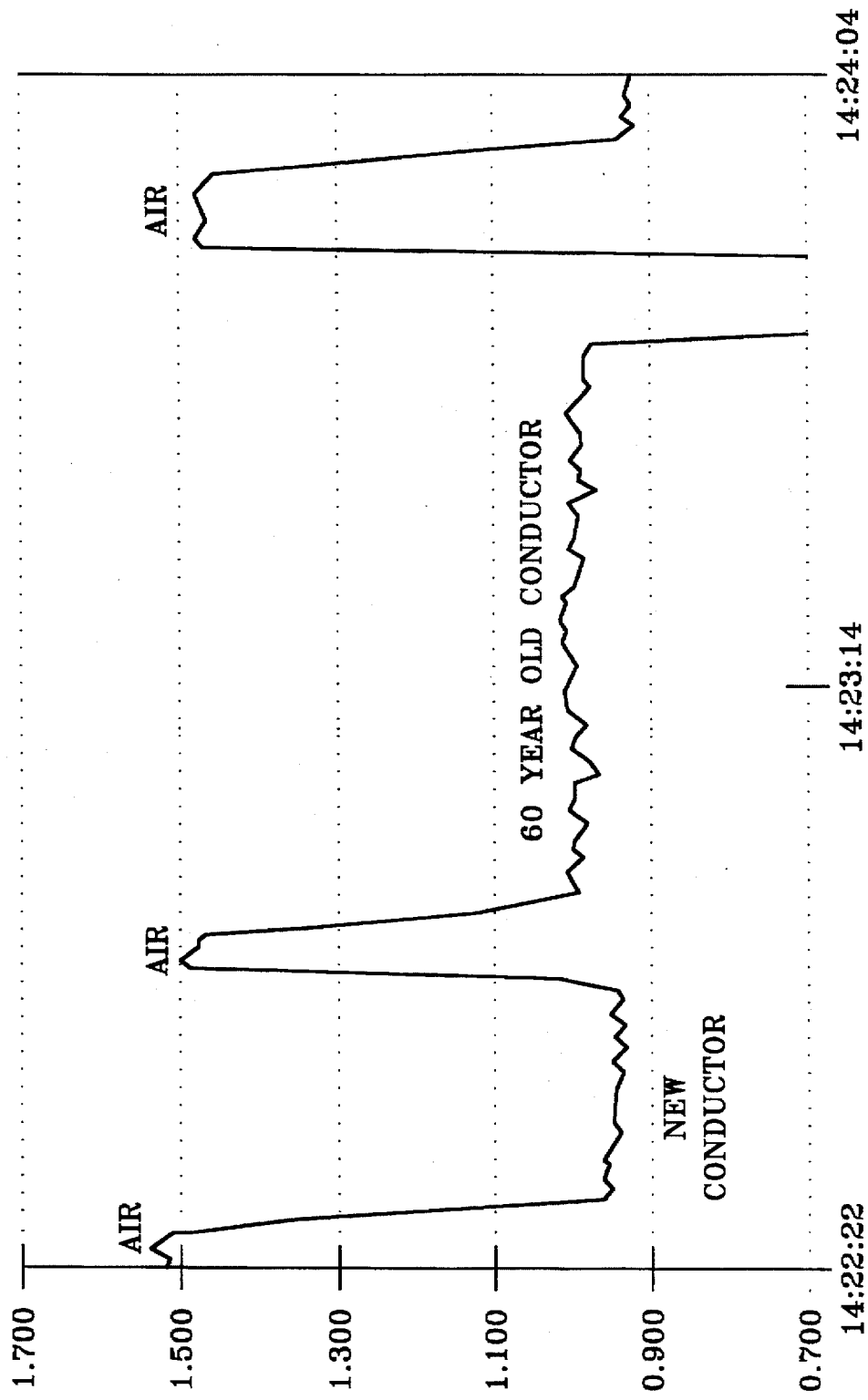
FIG. 9 is a printout of data recorded and printed by the data collection component of the invention and further illustrates the effect of amplification on the inventive device when compared to FIG. 4C.

Referring to FIG. 9, an analysis of a 60 year old conductor was analyzed immediately following the analysis of a new conductor. The two analyses were performed consecutively in time with the same system and components and the same data recording time base and parameters. The difference with respect to the elevation of the horizontal regions of the graphs is attributable to the amount of strength loss (e.g., corrosion, etc.) in the 60 year old conductor as it relates to the new conductor of identical original geometry.

Figure 10:
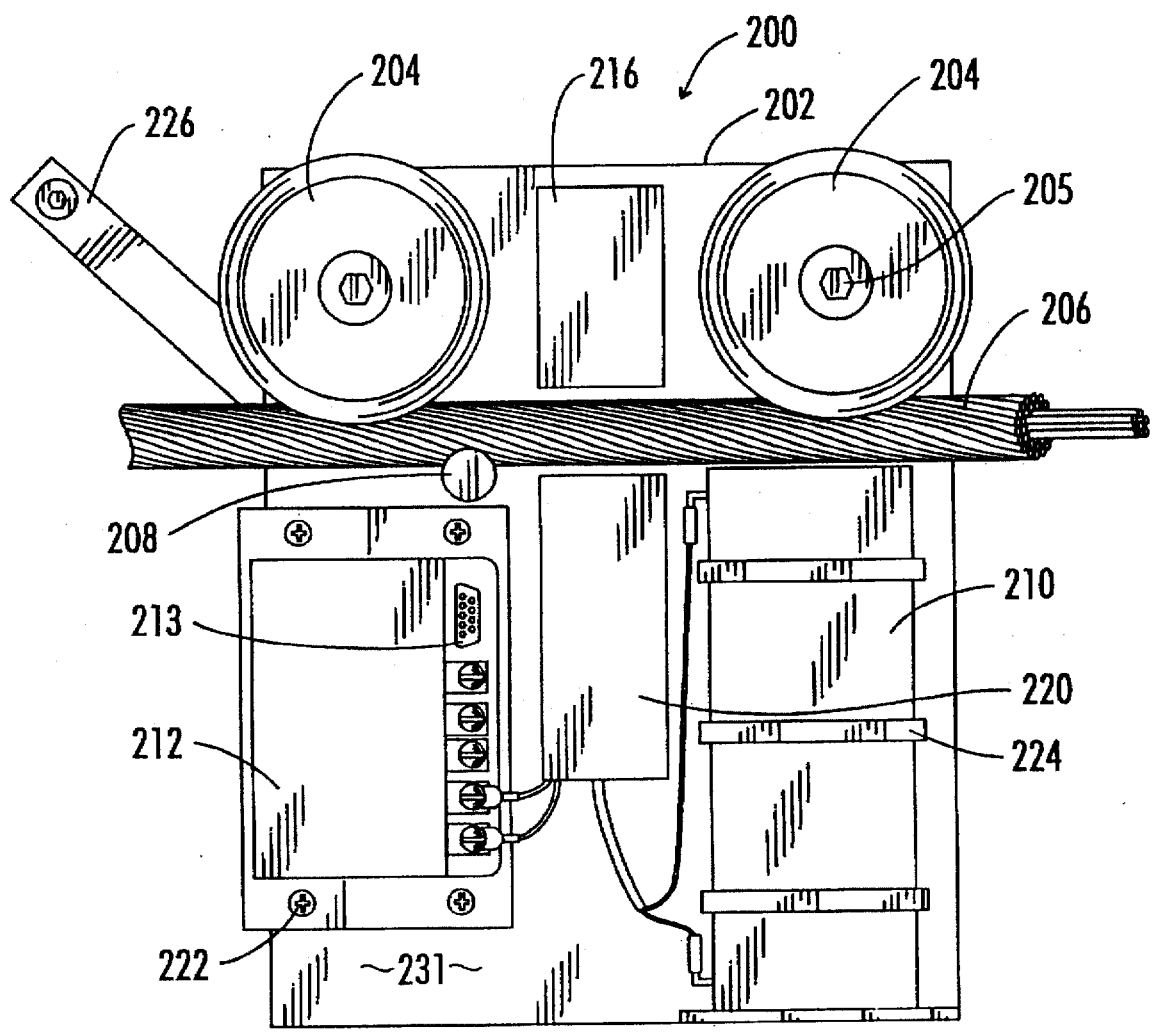
FIG. 10 is a front perspective view of an alternate embodiment of the inventive apparatus.
Figure 11:
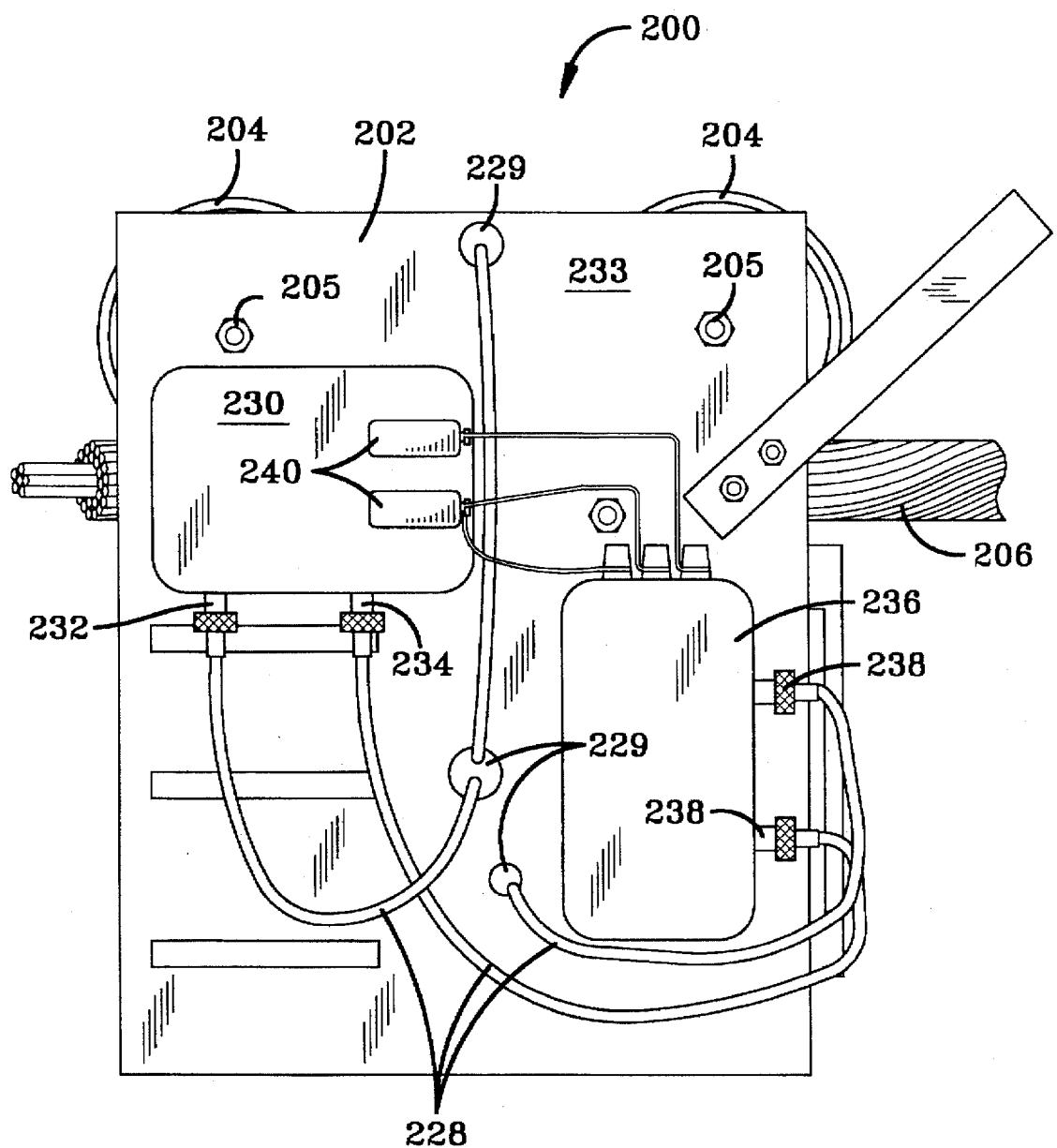
FIG. 11 is a back perspective view of the embodiment of the inventive apparatus shown in FIG. 10.
Figure 12:
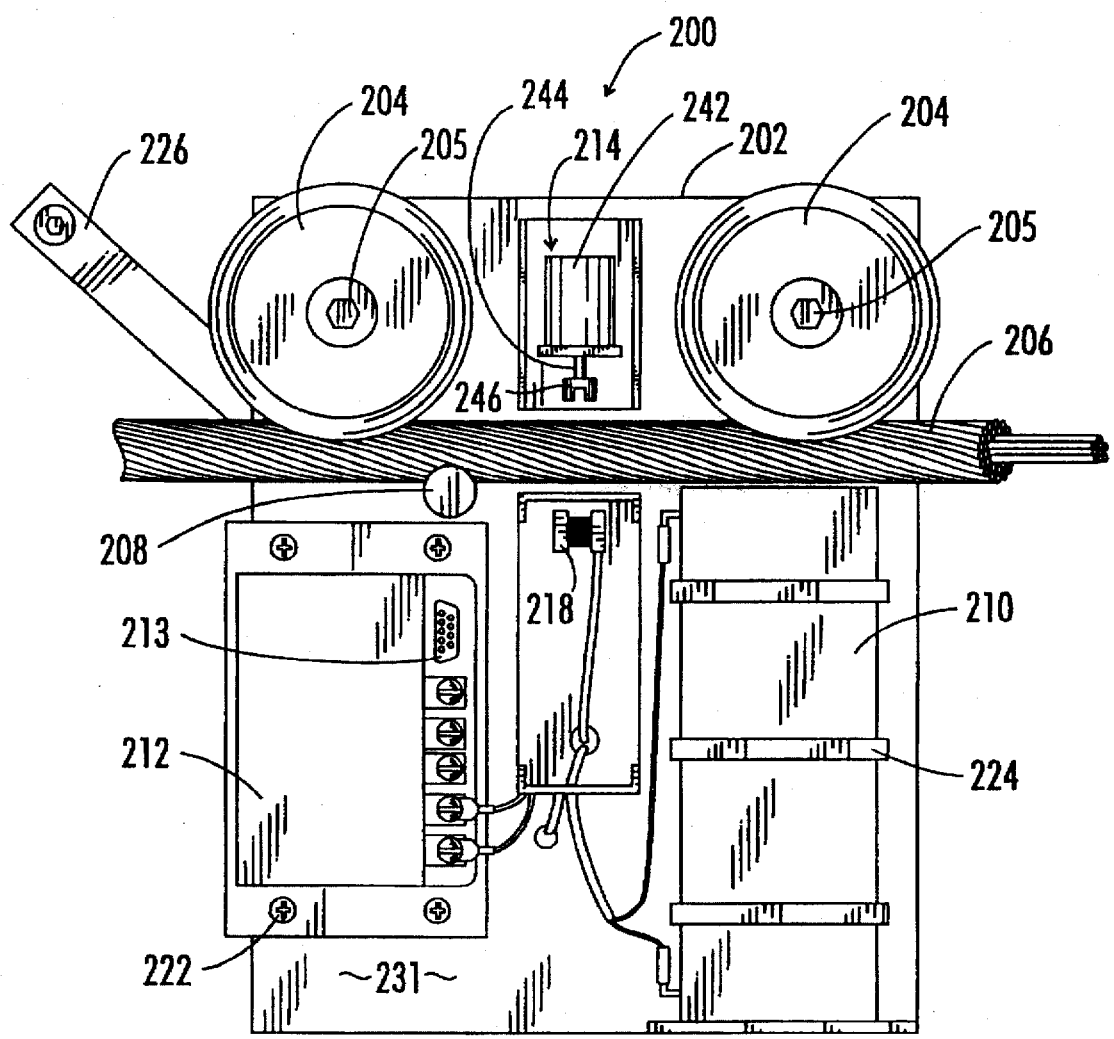
FIG. 12 is a front perspective view of the embodiment of the inventive apparatus shown in FIG. 10 with the coil cover and the cover for the magnetic source and motor combination removed.

With reference to FIGS. 10–12, an alternate embodiment of the present invention is illustrated and designated generally by the reference numeral 200. Embodiment 200 comprises a base 202 to which a pair of spaced apart alignment wheels 204 are attached via axles 205. The alignment wheels 204 are preferably aligned in a parallel relationship to enable the conductor 206 to lie along a plane parallel to both alignment wheels 204.

Tensioner 208 is provided to maintain the conductor 206 in an engaging relationship with the alignment wheels 204. Hence, the alignment wheels 204 further include an annular conductor receiving torus around the body of each alignment wheel 204.

Battery 210, data recording device 212 having a serial port of the type RS-232 (e.g., a Telog analog data recorder model 2101-62), magnetic source 214 shrouded by magnetic source cover 216, coil 218 and coil cover 220 are all removably or permanently attached to the base 202 by, for example, fasteners 222, or attachment bands 224 (FIGS. 10–12). Tongue 226 is pivotally or rigidly attached to the base 202 to enable the base 202 and its various components to be towed by a tug similar or different than that described above and shown in FIG. 1.

With reference to FIG. 11, shielded conductors 228 (e.g., model R6-58 AU) are attached to the operational amplifier 230 having an input terminal 232 and an output terminal 234, and a peak hold storage device 236. Base 202 has optional apertures 229 to enable the shielded conductors 228 to pass from a front surface 231 to a back surface 233 of the base 202. The peak hold device 236 further includes signal terminals 238 which in turn are interconnected to a battery store provided to supply the operating power for the operational amplifier 230 and the peak hold device 236.

With reference to FIG. 12, the covers 216 and 220 have been removed from the magnetic source 214 and coil 218 respectively. In a manner similar to that described above, the magnetic source 214 further includes a motor 242 having a motor shaft 244 to which a magnet 246 is attached and allowed to rotate with the rotation of the shaft 244. Coil 218 is preferably a 300 turn coil of #29 wire.

These and other embodiments, and equivalents, of the present invention shall become apparent after consideration of the specification and drawings. All such alternate embodiments and equivalents are believed to be, and are contemplated as, part of the present invention whose only limitation is the scope of the appended claims.

What is claimed is:

1. An apparatus for detecting a loss of structural strength in a generally cylindrical conductor having a length and at least one metallic reinforcing member extending along the length of said conductor capable of exhibiting magnetic properties, comprising:

a rotatable source of magnetic energy configured to emanate a rotating magnetic field;

a coil winding mounted in a predetermined spaced relationship opposite from the source of magnetic energy defining a receiving space therebetween, wherein the receiving space is configured to receive said conductor having at least one metallic reinforcing member in spaced relationship between the source of magnetic energy and said coil winding to enable the rotating magnetic field emanating therefrom to induce a measurable voltage within the coil winding;

a rotatable member operatively mounted on said detector apparatus for biased, force-transmitting engagement on said conductor to movably support said detector apparatus for longitudinal movement along the length of said conductor and align said receiving space in a predetermined position relative to the longitudinal axis of said conductor.

2. A system for detecting a loss of cross-sectional area and the residual strength of a conductor having at least one metallic reinforcing member having magnetic properties comprising;

a detector component;

a data acquisition component;

a tug capable of providing a motive force to the detector component and linked to the detector component and the data acquisition component;

a source of power operatively connected to the tug, to enable said tug, detector component and data acquisition component to travel along a conductor;

the detector component further includes a rotatable mounted permanent magnet positioned to emanate a magnetic field toward a coil winding spaced apart therefrom and defining a conductor receiving space therebetween, and a drive element connected to said magnet to impart a rotational torque upon said magnet to enable the coil winding to experience an induced voltage in response to the rotating magnetic field.

3. The system of claim 2, wherein:

the at least one metallic reinforcing member having magnetic properties and partially comprised of a material selected from the group of materials consisting of steel, iron, nickel, and cobalt.

4. The system of claim 2, further including:

a recorder to record the voltage induced in the coil winding.

5. The system of claim 4, further including:

connection means for electronically interconnecting the recorder to the coil winding.

6. The system of claim 5, such that the connection means further includes:

a transmitter and a receiver to transmit voltage information from the coil to the recorder by a radio frequency carrier signal and without the need for wiring to interconnect the recorder to the coil winding.

7. The system of claim 2, further including:

a housing to cover the coil winding and the source of magnetic energy.

8. The system of claim 2, further comprising:

a power source for energizing the drive element.

9. The system of claim 2, further comprising: an operational amplifier to alter the electronic signal induced into the coil.

10. The system of claim 2, further comprising:

a peak hold device for recording maximum voltages per a user selected unit of time.

11. The system of claim 2, such that the source of magnetic energy further comprises:

a magnet having a positive pole substantially parallel to a negative pole.

12. The system defined in claim 2 wherein said magnet has a positive pole disposed substantially parallel to a negative pole and wherein said poles are disposed at generally a right angle to a conductor disposed longitudinally within said receiving space.

13. An apparatus for detecting a loss of structural strength of a generally cylindrical conductor having a length and at least one metallic member having magnetic properties, comprising in combination;

a detector component;

a data acquisition component linked to said detector component;

the detector component further including a rotatably mounted permanent magnet and a spaced, oppositely disposed coil winding defining a receiving space for said conductor and a drive element operatively connected to said magnet to impart a rotational torque upon said magnet;

a mounting component operatively connected to said detector component and said data acquisition component and including a pair of spaced and oppositely disposed mounting members configured to receive said conductor in force-transmitting, movable engagement to support said detector and data acquisition components for longitudinal movement along the length of said conductor when said conductor is disposed in said receiving space in essentially the same relative position between said magnet and coil winding;

and a source of motive power operatively connected to one of said mounting component, said detector component and said data acquisition component to effect travel of said apparatus along the length of said conductor.

14. The apparatus defined in claim 13 wherein said conductor includes a plurality of discrete metallic strands having magnetic properties and arranged in a closely adjacent generally cylindrical configuration.

* * * * *